US010888345B2

(12) United States Patent
Eads et al.

(10) Patent No.: US 10,888,345 B2
(45) Date of Patent: Jan. 12, 2021

(54) CAPTURE DEVICES

(71) Applicant: Boston Scientific Scimed, Inc., Maple Grove, MN (US)

(72) Inventors: Daniel L. Eads, Solsberry, IN (US); Eric D. McLeish, Bloomington, IN (US); Tyler Bylsma, Wyoming, MI (US); Raymond G. Amos, III, Spencer, IN (US); Mark A. Voss, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 288 days.

(21) Appl. No.: 15/951,468

(22) Filed: Apr. 12, 2018

(65) Prior Publication Data

US 2018/0296234 A1    Oct. 18, 2018

Related U.S. Application Data

(60) Provisional application No. 62/484,989, filed on Apr. 13, 2017.

(51) Int. Cl.
*A61B 17/221* (2006.01)
*A61B 90/00* (2016.01)

(52) U.S. Cl.
CPC ............ *A61B 17/221* (2013.01); *A61B 90/03* (2016.02); *A61B 2017/2212* (2013.01)

(58) Field of Classification Search
CPC ............ A61B 17/221; A61B 17/22031; A61B 17/2909; A61B 2017/2212;

(Continued)

(56) References Cited

U.S. PATENT DOCUMENTS 5,817,104 A    10/1998  Bilitz et al.
5,924,715 A    7/1999   Lippitt et al.
(Continued)

FOREIGN PATENT DOCUMENTS

WO    2016/061297 A1    4/2016
WO    2016/209318 A1    12/2016

OTHER PUBLICATIONS

International Search Report and Written Opinion dated Jun. 18, 2018 in International Application No. PCT/US2018/027249 (15 pages).

*Primary Examiner* — Mohamed G Gabr
(74) *Attorney, Agent, or Firm* — Bookoff McAndrews, PLLC

(57) ABSTRACT

Numerous devices are described. One device may comprise: a handle including a wire attachment portion; an actuator movably mounted to the handle, the actuator including a reaction chamber; a plunger movably mounted to the actuator, the plunger including a distal stop with a sheath attachment portion, and a proximal stop located in the reaction chamber; a resilient element including a distal end attached to the proximal stop, and a proximal end movable relative to plunger; and a force reduction element located in the reaction chamber between the resilient element and a reaction surface in the cavity. The resilient element may bias the plunger distally relative to the actuator, and be compressed when a proximally-directed force is applied to the plunger. The force reduction element may dissipate a portion of the proximally-directed force. Related devices and methods are also described.

18 Claims, 6 Drawing Sheets

(58) Field of Classification Search
CPC .. A61B 2017/2215; A61B 2017/22035; A61B 2017/305; A61B 90/03
See application file for complete search history.

(56) References Cited

U.S. PATENT DOCUMENTS

| | | |
|---|---|---|
| 2003/0225419 A1 | 12/2003 | Lippitt et al. |
| 2013/0053863 A1* | 2/2013 | Juravic ................. A61B 5/227 606/119 |
| 2015/0327878 A1* | 11/2015 | Chu ....................... A61B 90/03 606/127 |
| 2016/0199079 A1 | 7/2016 | Chu et al. |

* cited by examiner

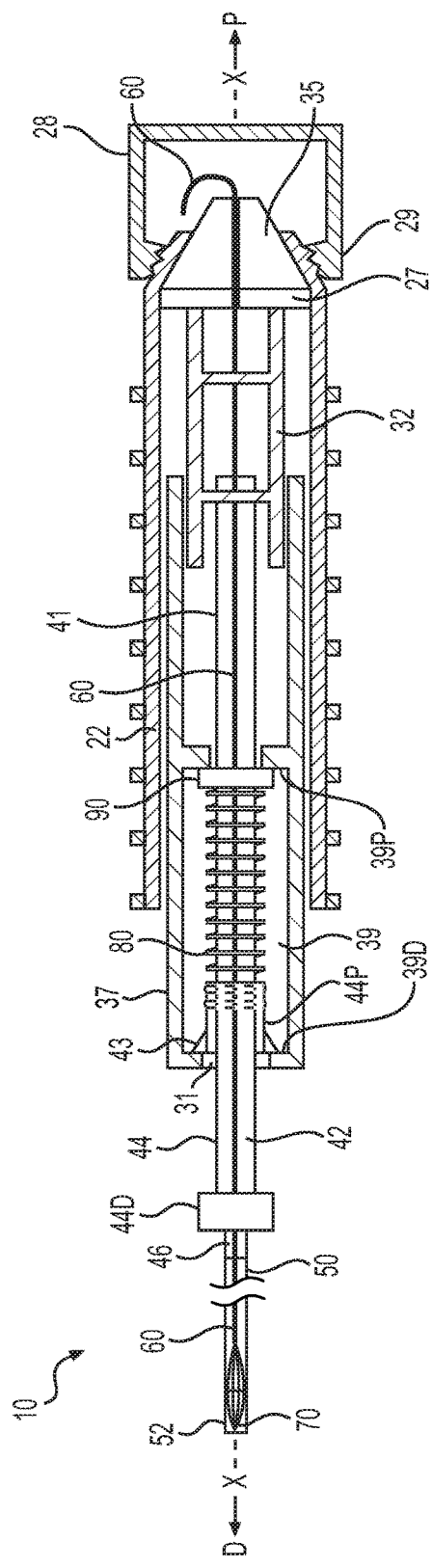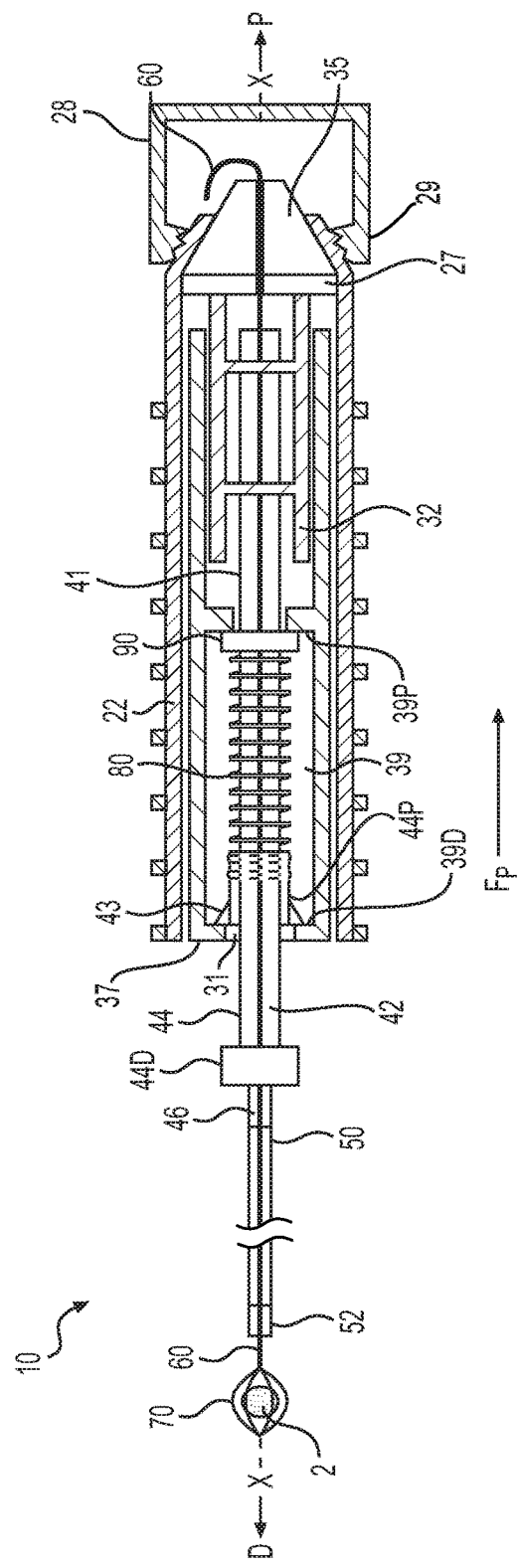

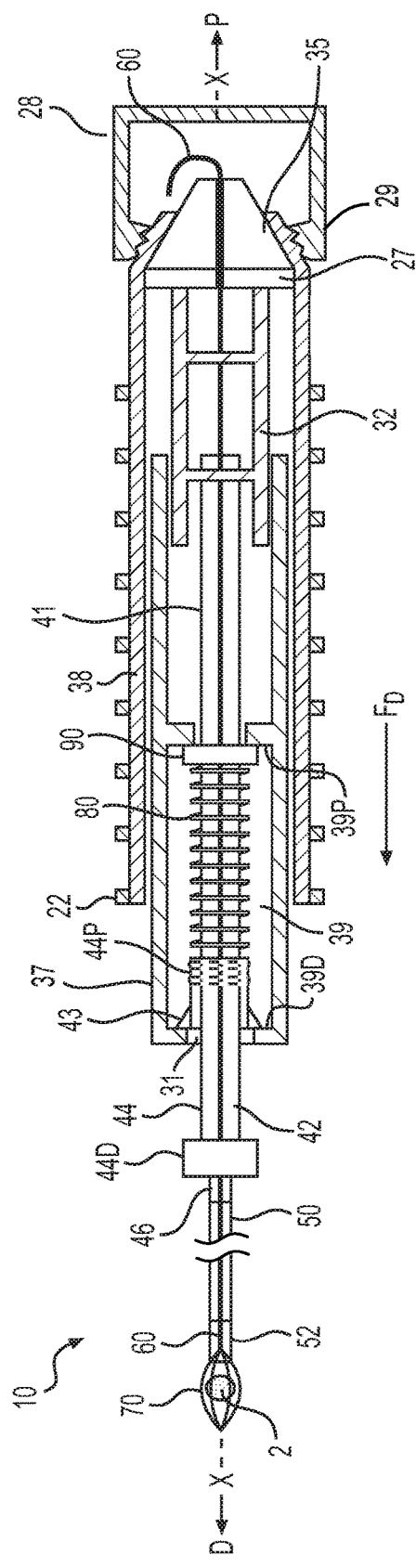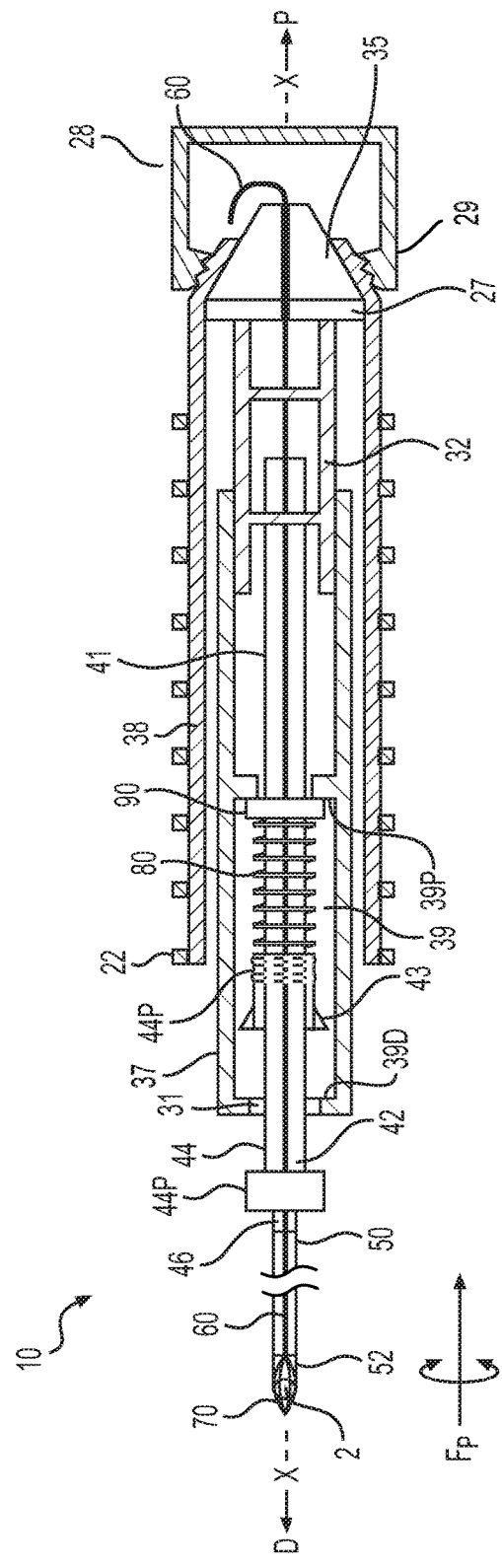
FIG. 3C
FIG. 3D

CAPTURE DEVICES

CROSS-REFERENCE TO RELATED APPLICATIONS

This application claims the benefit of priority to U.S. Provisional Application No. 62/484,989, filed Apr. 13, 2017, which is incorporated by reference herein in its entirety.

TECHNICAL FIELD

Aspects of the present disclosure generally relate to medical devices and procedures. Particular aspects relate to capture devices.

BACKGROUND

During noninvasive procedures, a physician may use a capture device (e.g., a basket or grasper) to engage objects in a body. For example, in some urology procedures, the physician may advance a sheath into a kidney, extend a basket from the sheath, engage a stone in the kidney with the basket, and retract the basket to capture the stone. A plurality of stones and/or stone fragments may need to be removed during the procedure, requiring the basket to be extended numerous times. Repetitive use of the basket may damage the sheath. For example, the basket may be expanded by the stone, such that retracting the basket even partially into the sheath imparts a considerable force to the sheath, such as a radially-directed force and/or a proximally-directed force. Over time, the radially-directed force may cause the sheath to tear open, rendering the device inoperable; and the proximally-directed force may cause the sheath to buckle, again rendering the device inoperable.

These problems can increase costs by reducing the useful life of the sheath. Moreover, if the sheath tears or buckles during a procedure, then the surgeon may need to advance other tools into the kidney to remove the stone and/or the capture device, further increasing costs. If the capture device cannot be safely removed, then an invasive procedure may be required, even further increasing costs. Aspects of this disclosure may remedy these difficulties, and/or address other aspects of the prior art.

SUMMARY

One aspect of the present disclosure is a device. Examples of this device may comprise: a handle including a wire attachment portion; an actuator movably mounted to the handle, the actuator including a reaction chamber; a plunger movably mounted to the actuator, the plunger including a distal stop with a sheath attachment portion, and a proximal stop located in the reaction chamber; a resilient element located in the reaction chamber, the resilient element including a proximal end movable relative to plunger; and a force reduction element located in the reaction chamber between the proximal end of the resilient element and a proximal surface of the reaction chamber. The resilient element may bias the plunger distally relative to the actuator. The resilient element may be compressible when a proximally-directed force is applied to the plunger. And the force reduction element may dissipate an amount of the proximally-directed force.

In some aspects, a distal end of the resilient element may be attached to the proximal stop. The force reduction element may be movable relative to actuator and the resilient element. The device may further comprise a shaft extending proximally from the proximal stop, and the force reduction element may be movably mounted on the shaft. For example, the force reduction element may include an annular shape with an opening, and the shaft may extend through the opening. In some aspects, the actuator may be made of a first material, the resilient element may be made of a second material, the force reduction element may be made of a third material, and a coefficient of friction between the first and second materials may be greater than a coefficient of friction between the second and third materials. For example, the first material may be polymeric and at least one of the second or third materials may be metallic. At least one of the second or third materials may include a lubricious coating or friction-reducing surface treatment.

According to one aspect, the device may be configured such that, prior to application of the proximally-directed force, the resilient element assumes an expanded configuration where (i) the proximal stop of the plunger maintains contact with a distal surface of the reaction chamber, (ii) the proximal end of the biasing element maintains contact with a distal surface of the force reduction element, and (iii) a proximal surface of the force reduction element maintains contact with a proximal surface of the reaction chamber. The actuator may be movable relative to the handle to extend or collapse the end-effector without compressing the resilient element. And the proximally-directed force may cause the resilient element to assume a compressed configuration where the distal stop is spaced apart from the distal surface of the reaction chamber. The resilient element may be a spring with a circular cross-sectional area; and a proximal end of the spring may define a contact surface consisting of outer surfaces of the circular cross-sectional area of the spring. At least the proximal end of the resilient element may include a lubricious coating or friction-reducing surface treatment.

The plunger may include a body extending longitudinally between the proximal and distal stops. The distal end of the actuator may include an opening, and the body may be movably mounted in said opening. For example, an exterior guide surface of the body of the plunger may be movable on an interior guide surface of the opening of the actuator, and at least one of said exterior and interior guide surfaces may be configured to reduce an amount of the proximally-directed force required to move the plunger relative to the actuator. At least the exterior guide surface may include a lubricious coating or friction-reducing surface treatment. In other aspects, the device may comprise: a sheath extending distally from the sheath attachment portion; a wire extending distally from the wire attachment portion and through the actuator, the plunger, and a distal end of the sheath; and a force transfer element attached to or embedded in the distal end of the sheath.

Another disclosed aspect is another device. Examples of this device may comprise: a handle including a wire attachment portion; an actuator movably mounted to the handle, the actuator including a reaction chamber; a plunger movably mounted to the actuator, the plunger including a distal stop with a sheath attachment portion, and a proximal stop located in the reaction chamber; a sheath extending distally from the sheath attachment portion; a wire extending distally from the wire attachment portion and through the actuator, the plunger, and the sheath; an end-effector located at a distal end of the wire; a resilient element located in the reaction chamber, the resilient element including a proximal end movable relative to plunger; and a force reduction element located in the reaction chamber between the resilient element and a reaction surface of the reaction chamber. The actuator may be movable proximally relative to the handle to expand the end-effector out of the sheath, and distally relative to the handle to collapse the end-effector into the sheath. The end-effector may apply a proximally-directed force to the sheath when the actuator is moved distally to collapse end effector around an object. And the force reduction element may dissipate of an amount of the proximally-directed force.

Accordingly, the device may be configured such that, prior to the application of the proximally-directed force, the resilient element may assume an expanded configuration where (i) the proximal stop of the plunger maintains contact with a first reaction surface of the reaction chamber, (ii) the proximal end of the biasing element maintains contact with a distal surface of the force reduction element, and (iii) a proximal surface of the force reduction element maintains contact with a second reaction surface of the reaction chamber. The actuator may be movable relative to the handle to extend or collapse the end-effector without compressing the resilient element. The proximally-directed force may cause the resilient element to assume a compressed configuration where the proximal stop is spaced apart from the first reaction surface.

The force reduction element may be movably mounted in the reaction chamber. A guide surface of the plunger may be movable on a guide surface of the actuator, and at least one of said guide surfaces may include a lubricious coating or friction-reducing surface treatment. According to one aspect, a distal end of the sheath may include a force transfer element attached to or embedded in a distal end of the sheath. For example, the force transfer element includes at least one of a ring, a coil, or a wire attached to or embedded in a distal end of the sheath. The force transfer element may, in some aspects, be expandable with the distal end of the sheath.

Yet another disclosed aspect is a device. Examples of this device may comprise: a handle including a wire attachment portion; an actuator movably mounted to the handle, the actuator including a reaction chamber and a guide surface; a plunger movably mounted to the actuator, the plunger including a distal stop with a sheath attachment portion, a proximal stop located in the reaction chamber, a guide surface movable on the guide surface of actuator, and a shaft extending proximally from said proximal stop; a resilient element movably mounted on the shaft in the reaction chamber, the resilient element including a proximal end movable relative to the plunger and the shaft; a sheath extending distally from the sheath attachment portion; a wire extending distally from the wire attachment portion, through the shaft and the plunger, and into the sheath; a basket located at a distal end of the wire; and a force reduction element located in the reaction chamber between the resilient element and a reaction surface of the reaction chamber. For example, the actuator may be movable proximally relative to the handle to expand the basket out of the sheath, and distally relative to the handle to collapse the basket into the sheath. The basket may apply a proximally-directed force to the sheath when the actuator is moved distally to collapse the basket around an object. The sheath may transfer the proximally-directed force to the plunger. The plunger may transfer the proximally-directed force into the resilient element. And the force reduction element may dissipate of an amount of the proximally-directed force.

Accordingly, one of the guide surface of the actuator and the guide surface of the plunger may be configured to reduce an amount of the proximally-directed force required to move the plunger relative to the actuator. For example, the sheath may be configured to transfer the proximally directed force into the plunger without buckling; and/or a distal end of the sheath may be configured to transfer the proximally directed force into the sheath without expanding a diameter of said distal end.

It is understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written description herein, serve to explain this disclosure. Each drawing depicts one or more aspects of this disclosure, as follows:

FIGS. 3A-D depicts section views of the FIG. 1 device taken along a section line 3-3 depicted in FIG. 2.

DETAILED DESCRIPTION

Aspects of various capture devices are now described. Some aspects are described with reference to noninvasive procedures, such as urology procedures, wherein a sheath is advanced to a treatment site, and a capture device is extended from the sheath to engage an object at the treatment site. In urology procedures, for example, the sheath may be inserted into the urethra, moved through the bladder and ureter, and advanced into a calyx of a kidney; and the capture device may be extended distally from the sheath to engage one or more stones and/or stone fragments located in the calyx. References to a particular type of procedure, such as a urology procedure; capture device, such as a basket or grasper; organ, such as a kidney; and/or object, such as a stone or stone fragment, are provided for convenience and not intended to limit this disclosure. Accordingly, the concepts described herein may be utilized for any analogous device or system.

Numerous axes and directions are described. Each axis may be transverse, or even perpendicular, with the next so as to establish a Cartesian coordinate system with an origin point O. One axis may extend along a longitudinal axis of an element. The terms "proximal" and "distal" may be used to indicate a direction along any axis. Proximal refers to a position closer to the exterior of the body or a user, whereas distal refers to a position closer to the interior of the body or further away from the user. Appending the initials "P" or "D" to an element number signifies a proximal or distal location or direction. The term "elongated" may refer to any object that is longer in relation to its width, such as an object having a length that is at least two times longer than its width along its longitudinal axis. Some elongated objects, for example, are axially extending in a proximal or distal direction along a central longitudinal axis. Unless claimed, these terms are provided for convenience and not intended to limit this disclosure to a particular location, direction, or orientation.

As used herein, terms such as "comprises," "comprising," or like variations, are intended to cover a non-exclusive inclusion, such that any aspect that comprises a list of elements does not include only those elements or steps, but may include other elements or steps not expressly listed or inherent thereto. Unless stated otherwise, the term "exemplary" is used in the sense of "example" rather than "ideal." Conversely, the terms "consists of" and "consisting of" are intended to cover an exclusive inclusion, such that an aspect that consists of a list of elements includes only those elements. As used herein, terms such as "about," "substantially," "approximately," or like variations, indicate a range of values within +/−5% of a stated value.

Figure 1:
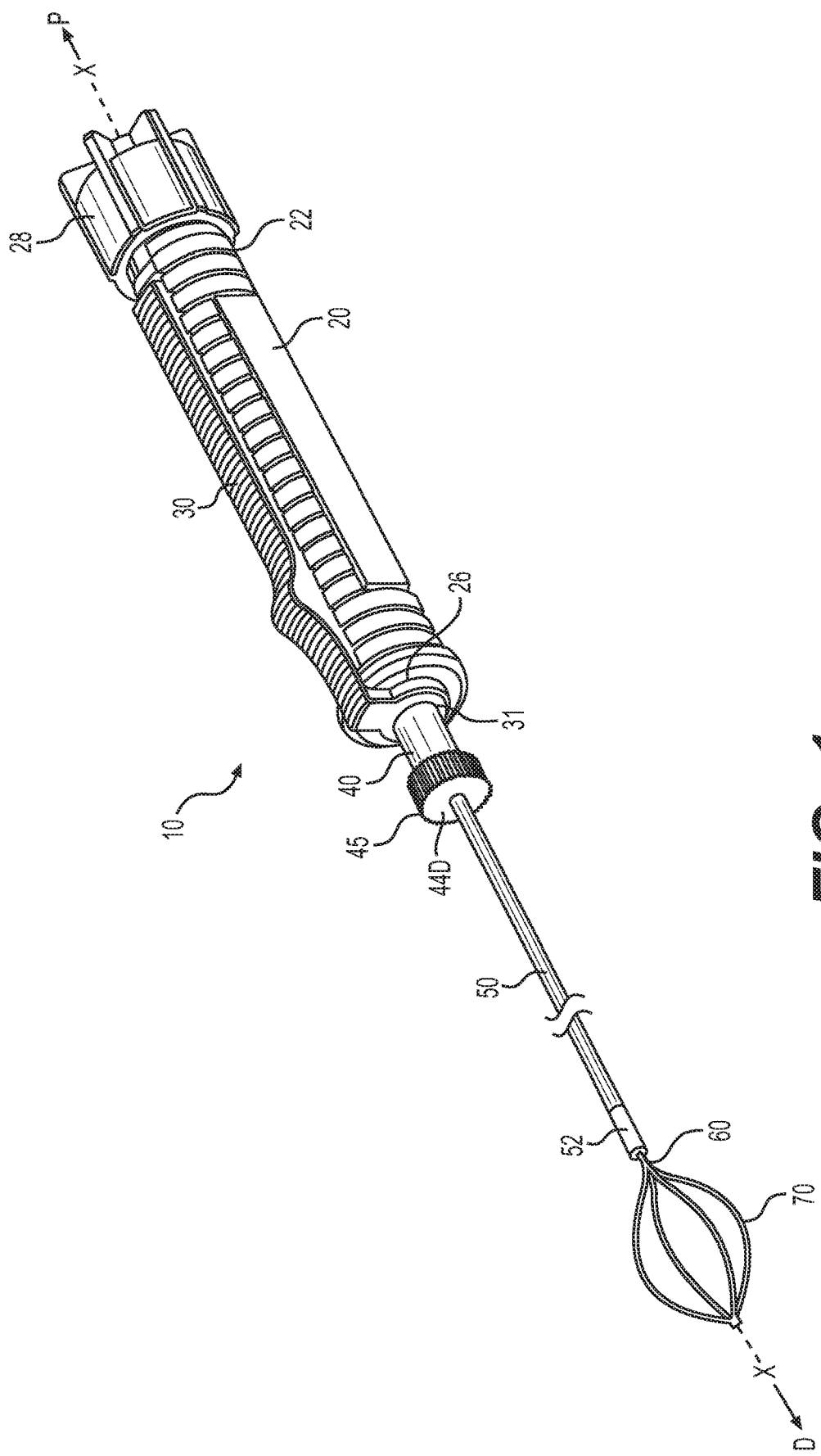
FIG. 1 depicts an assembled view of exemplary device.
Figure 2:
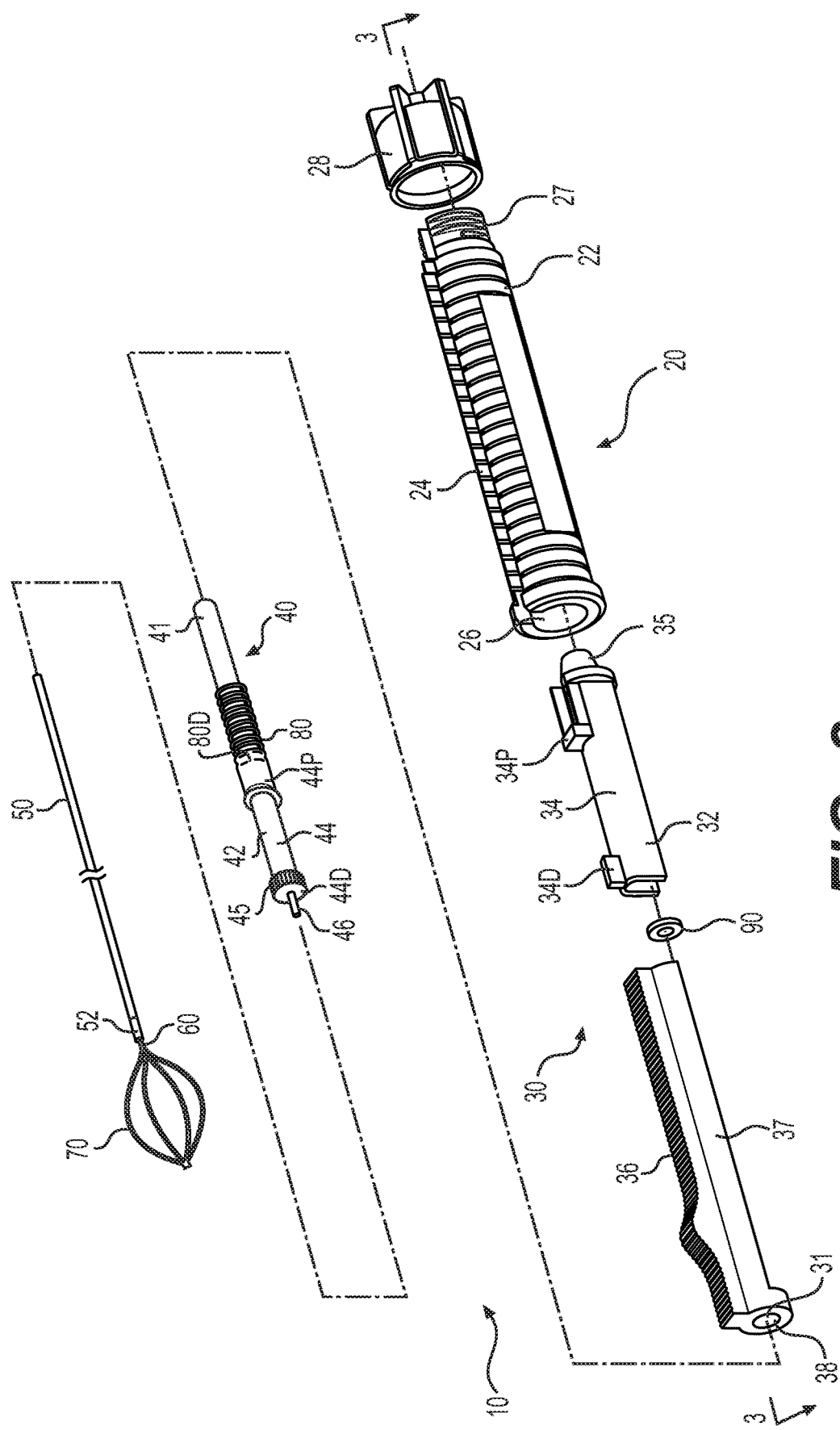
FIG. 2 depicts an exploded view of the FIG. 1 device.

An exemplary device or capture 10 is depicted in FIG. 1. As shown, device 10 may comprise: a handle 20; an actuator 30 movably mounted to handle 20; and a plunger 40 movably mounted to actuator 30. A sheath 50 may be attached to plunger 40. A wire 60 may extend distally through handle 20, actuator 30 and plunger 40 from handle 20; and an end-effector 70 may be attached to a distal end of wire 60. As shown in FIG. 2, a resilient element 80 may be located in actuator 30, and a force reduction element 90 may be located on or adjacent plunger 40. Actuator 30 may be operable to extend end-effector 70 distally out of sheath 50 to surround a stone 2, and retract end-effector 70 proximally into sheath 50 to capture the stone 2. Depending upon size, either stone 2 and/or end-effector 70 may apply forces to sheath 50 while capturing stone 2. Force reduction element 90 may help to enhance the durability of device 10 by mitigating the applied forces. For example, element 90 may be configured to dissipate at least a portion of the applied forces. In some aspects, these forces are dissipated by reducing frictional forces associated with, for example, independent movements of plunger 40 and sheath 50 relative to handle 20, actuator 30, and wire 60.

Handle 20 may be grasped in a hand of a user and/or attached to another medical device. As shown in FIGS. 1 and 2, handle 20 may comprise: a body 22 extending along a longitudinal axis X-X of device 10. Body 22 is depicted in FIGS. 1-2 as having a cylindrical shape, although any shape may be used. The exterior surfaces of body 22 may be contoured to define a grip surface. Channel 24 may extend through body 22 along axis X-X. In FIG. 2, for example, the distal end of body 22 includes an opening 26, and the proximal end of body 22 includes a wire attachment portion comprising a vise 27 with a pair opposing arms, and a cap 28 that is removably engageable with vise 27 and/or body 22 to close the opposing arms together. As shown in FIGS. 3A-D, cap 28 may be attached to body 22 by a threaded connection 29.

Actuator 30 may be configured to move sheath 50 in a proximal-distal direction along longitudinal axis X-X. As shown in FIG. 2, actuator 30 may comprise a body 32 with a guide surface 34, and a slider 36 movable along guide surface 34. Body 32 may be removably attached to handle 20. For example, body 32 of FIG. 2 comprises an attachment portion 35 shaped for receipt between the opposing arms of vise 27. Body 32 may be removably attached to handle 20 by placing attachment portion 35 between the opposing arms of vise 27, and engaging cap 28 with vise 27 via threaded connection 29 until said opposing arms are closed around attachment portion 35. As in FIG. 2, body 32 may have a U-shaped cross-section, defining a partially open lumen extending through body 32 along axis X-X. Other cross-sectional shapes may be used, including closed perimeter shapes, such as a circular shape.

Slider 36 may be moveable on or relative to guide surface 34 between closed or open positions corresponding with closed or open configurations of end-effector 70. As shown in FIG. 2, for example, slider 36 may include a body 37 extending along longitudinal axis X-X, and a channel 38 extending longitudinally through body 37. Channel 38 may be configured to receive a distal portion of body 32 of actuator 30, allowing body 37 of slider 36 to move (e.g., slide) along guide surface 34. Channel 38 of FIG. 2 includes an open portion, allowing portions of plunger 40 to be visible from the underside. As shown in FIG. 2, guide surface 34 may include a distal stop 34D and a proximal stop 34P. As shown in FIGS. 3A-3D, body 32 of actuator 30 may be received in channel 38 so that interior stop surfaces of body 32 are engageable with distal and proximal stops 34D and 34P to control movement of slider 36. For example, body 37 of slider 36 may be located in channel 24 of handle 20 so that an underside of body 37 slides along guide surface 34, allowing for movement of slider 36 between: (i) a distal or closed position, wherein distal stop 34D contacts an interior stop surface of channel 38 (e.g., as in FIGS. 2 and 3A); and (ii) a proximal or open position, wherein proximal stop 34P contacts the interior stop surface of channel 38 (e.g., as in FIGS. 2 and 3B). End-effector 70 may be retracted into sheath 50 when slider 36 is the closed position (e.g., FIG. 3A), and extended from sheath 50 when slider 36 is the open position (e.g., FIG. 3B).

Plunger 40 may be movably mounted to actuator 30 and configured to dissipate forces applied by sheath 50 and/or enable rotation of sheath 50. As shown in FIG. 2, for example, plunger 40 may comprise a body 42 with a guide surface 44 including a distal stop 44D and a proximal stop 44P. Distal stop 44D may comprise a sheath attachment portion 46 engageable with sheath 50. For example, portion 46 may fit over or received within a proximal end of sheath 50. Plunger body 42 may be receivable in a distal portion of channel 38. As shown in FIG. 2, for example, channel 38 may have a distal opening 31, and body 42 may be movably mounted in opening 31, allowing forces to be dissipated with, for example, independent movements of plunger 40 relative to actuator 30. Exemplary independent movements may include proximal-distal movements along axis X-X, and/or rotational movements about axis X-X. Some movements may be indirectly caused by stone 2, while other movements are directly caused by a user. For example, in FIG. 1, distal stop 44D of plunger 40 includes a grip surface 45. Sheath 50 may be attached to distal stop 44D so that grip surface 45 may be used to rotate sheath 50 independent of wire 60 and/or end-effector 70.

Wire 60 may be an elongated metallic element, such as a surgical wire, although any type of material may be used. End-effector 70 may be attached to a distal end of wire 60. In FIG. 1, for example, end-effector 70 is a closed-ended basket made of a shape memory metal (e.g., nitinol). End-effector 70 may also be an open-ended grasper, or like capture device. Accordingly, end-effector 70 may be operable between a closed position, wherein end-effector 70 is collapsed inside of sheath 50 (e.g., FIG. 3A); and an open position, wherein end-effector 70 automatically expands after being extended distally out of sheath 50 (e.g., FIG. 3B). Any type of end-effector 70 may be used with device 10, including any closed-ended configurations (e.g., a basket) or open-ended configurations (e.g., two or more opposing jaws).

As shown in FIGS. 3A-D, a portion of channel 38 may define a reaction chamber 39, and resilient element 80 may be located in reaction chamber 39. Resilient element 80 is configured to bias plunger 40 distally relative to actuator 30. As shown in FIG. 2, a distal end 80D of resilient element 80 may be attached to proximal stop 44P of plunger 40. Any means of attachment may be used, including heat-shrinking proximal portion of stop 44P over the distal end 80D, forming stop 44P around distal end 80D, and/or otherwise fusing stop 44P together with distal end 80D. As also shown in FIG. 2, a plunger shaft 41 may extend proximally from proximal stop 44P, and each of plunger 40, resilient element 80, and shaft 41 may be joined together as a pre-formed plunger assembly to simplify device 10. Resilient element 80 may extend proximally from proximal stop 44P along and/or around plunger shaft 41, as in FIG. 2, where element 80 coils around a distal portion of shaft 41 along axis X-X. A proximal end of resilient element 80 may move independent of shaft 41. In some aspects, resilient element 80 may be a metallic spring with an exterior diameter smaller than an interior diameter of reaction chamber 39, allowing element 80 to buckle and/or shift inside reaction chamber 39, around shaft 41, without ever generating additional friction forces from contact with the interior surfaces of reaction chamber 39.

Resilient element 80 may be compressible and expandable within reaction chamber 39 to dissipate forces applied to plunger 40. For example, resilient element 80 may be compressible in a proximal-direction direction to dissipate an amount of the proximally-directed forces applied to plunger 40 by sheath 50; and/or have a fixed or variable spring constant configured to dissipate said forces in a linear or non-linear manner. As shown in FIGS. 3A-D, force reduction element 90 may be located between the proximal end of resilient element 80 and a proximal surface 39P of reaction chamber 39. Prior to application of such forces, resilient element 80 may achieve equilibrium in an expanded configuration where (i) proximal stop 44P of plunger 40 maintains contact with distal surface 39D, (ii) the proximal end of resilient element 80 maintains contact with a distal surface of element 90, and (iii) a proximal surface of element 90 maintains contact with proximal stop surface 39P of reaction chamber 39. As shown in FIGS. 3A-D, resilient element 80 may assume any number of intermediate positions until stone 2 assumes a stable, captured position in end-effector 70.

The forces applied to plunger 40 by sheath 50 may be small and invariable, making the responsiveness of plunger 40 an important consideration. For example, numerous proximally-directed and/or rotational forces may be applied to sheath 50 as stone 2 shifts about within end-effector 70 prior to assuming the stable, captured position. If the initial force required to move plunger 40 is too high, then some portion of these forces will be absorbed by sheath 50, potentially leading to damage from repetitive stresses and strains. Force reduction element 90 helps to dissipate even these small and invariable forces by, for example, providing a limited coefficient of friction between the proximal end of element 80 and a distal-facing reaction surface 90 of force reduction element 90, and/or a limited coefficient of friction between a proximal-facing reaction surface of element 90 and proximal stop surface 39P of chamber 39. Numerous aspects of reduction element 90 are now described.

In some aspects, force reduction element 90 is movable relative to actuator 30 and resilient element 80 to reduce the initial force required to move plunger 40 by preventing stress concentrations, such as those otherwise resulting from even a temporary coupling of plunger 40 with actuator 30. Shaft 41 may extend proximally from proximal stop 44P of plunger 40, as noted above, and force reduction element 90 may be movably mounted on shaft 41. Element 90 of FIG. 2 includes an annular shape with an circular opening, and shaft 41 extends through the circular opening along longitudinal axis X-X, although element 90 and said opening may assume any shape.

The applied forces may include a rotational component. For example, resilient element 80 may buckle in response to a proximally-directed force, causing indirect rotational forces; or element 80 may be directly rotated in response to a rotational force applied to handle surface 45 by a user. Force reduction element 90 may be configured to dissipate an amount of these forces. For example, actuator 30 or a portion thereof (e.g., distal reaction surface 39D of reaction chamber 39) may be made of a first material; resilient element 80 may be made of a second material; force reduction element 90 may be made of a third material; and a coefficient of friction between the first and second materials may be greater than a coefficient of friction between the second and third materials. As a further example, the first material may be a polymeric material, such as PEEK; the second material may be a metallic material, such as stainless steel; and the third material may be configured to reduce the coefficient of friction between element 80 and 90. In some aspects, the third material may be a carbonic material (e.g., a carbon-rich material) configured to provide a low friction, low wear contact between the proximal end of resilient element 80 and proximal reaction surface 39P of reaction chamber 39. Any of the first, second, and/or third materials may likewise be applied to actuator 30, resilient element 80, and/or force reduction element 90 as a lubricious coating, such as Teflon® coating; or other friction-reducing surface treatment, such as a polished finish.

Additional aspects of device 10 may be further configured to dissipate forces applied to plunger 40 from sheath 50. Each additional aspect may be incorporated into any device 10 described herein, each possible variation being part of this disclosure.

According to one aspect, guide surface 44 of plunger 40 and/or distal opening 31 of channel 38 may be configured to limit a coefficient of friction between plunger 40 and actuator 30, further increasing the responsiveness of plunger 40 to small and/or invariable forces. In some aspects, guide surface 44 may be movable (e.g., rotatable and/or slidable) on an interior edge or surface of distal opening 31, and at least one of surface 44 and the interior edge or surface of opening 31 may be configured to reduce an amount of initial force required to move plunger 40, and/or reduce an amount of ongoing forces required to keep plunger 40 in motion until stone 2 settles into position. For example, the interior edge or surface of opening 31 may be narrowed to minimize a contact area with guide surface 44. Guide surface 44 and/or said interior edge or surface also may include a lubricious coating (e.g., a Teflon® coating), or other friction-reducing surface treatment (e.g., a smooth finish) configured to minimize a coefficient of friction between guide surface 44 and the interior edge or surface of opening 31.

Other aspects of resilient element 80 and/or force reduction element 90 may be similarly modified. For example, resilient element 80 may be a spring formed from an elongated wire having a circular cross-section; and the proximal end of said spring may define a contact surface consisting of outer surfaces (e.g., points tangential to) the circular cross-sectional area of the spring. In this configuration, the contact area between resilient element 80 and force reduction element 90 is limited to reduce an amount of frictional force generated by rotating element 80 directly against element 90. Any portion of element 80 may include a lubricious coating or other friction-reducing surface treatment configured to further reduce said forces. For example, at least proximal end 80P may include a Teflon® coating configured to reduce frictional forces; and/or element 80 may be metallic, and element 90 may include a carbonic coating configured to reduce said forces. In some aspects, all but sheath attachment portion 46 of plunger 40 may include the lubricious coating to further simplify device 10.

Figure 4A:
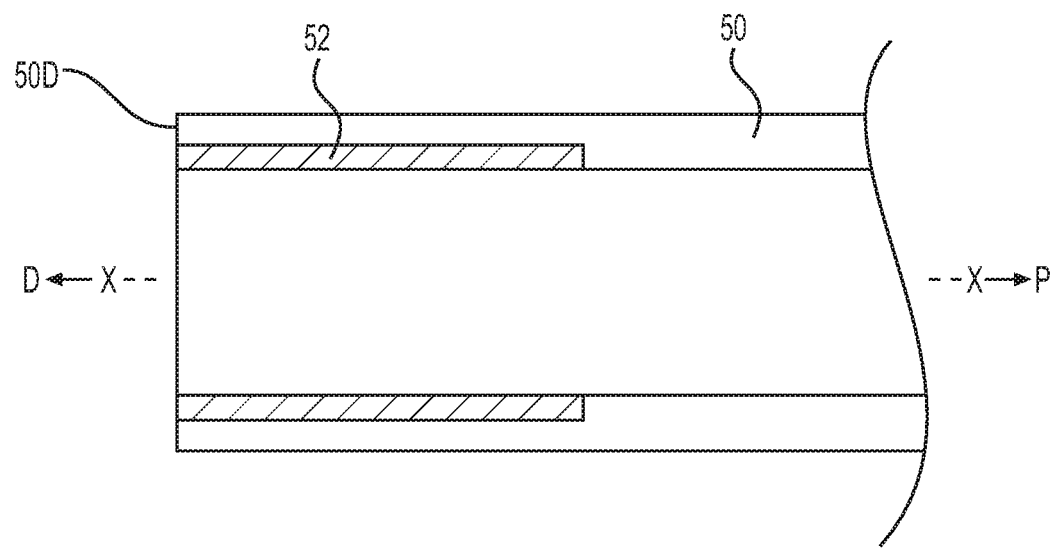
FIGS. 4A-B depicts section views of a distal end the FIG. 1 device.
Figure 4B:
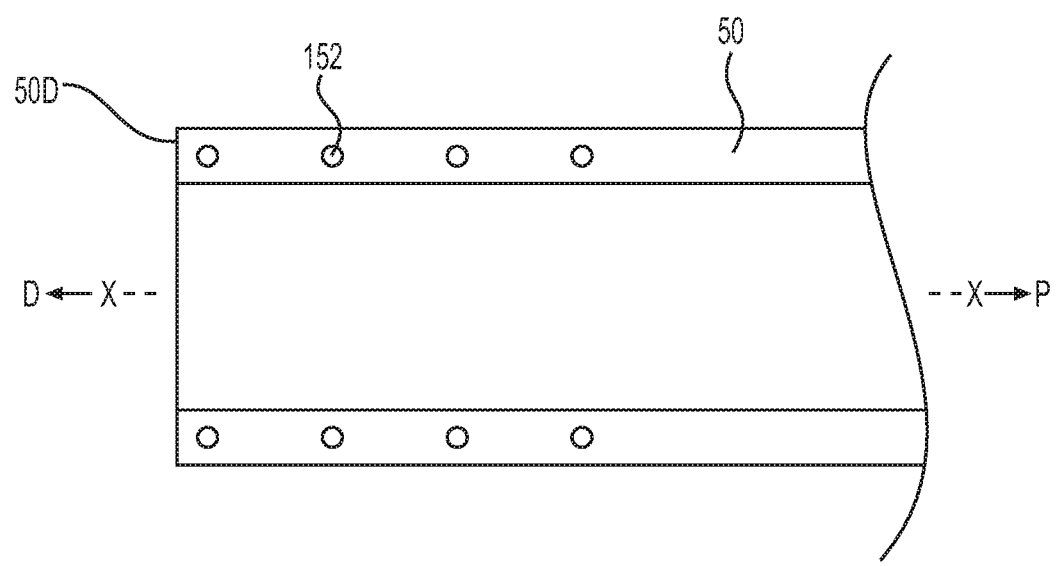

Aspects of sheath 50 may be configured for efficient force transfer. For example, a distal end 50D of sheath 50 may comprise a force transfer element 52, examples of which are depicted in FIGS. 4A-B. As shown in FIG. 4A, for example, force transfer element 52 may be a cylindrical element that is attached to or embedded in distal end 50D to (i) prevent expansion of sheath 50 when end-effector 70 and/or stone 2 is moved proximally; and (ii) more directly transfer any proximally-directed forces from end-effector 70 and/or stone 2 into sheath 50. Force transfer element 52 also may be configured to permit limited expansion of the distal end 50D, ensuring that at least some portion of 2 may be received in sheath 50. As shown in FIG. 4B, for example, another force transfer element 152 may include at least one of a ring, a coil, and a wire that is attached to or embedded in distal end 50D, and/or expandable relative to axis X-X with the distal end 50D of sheath 50.

Figure 5:
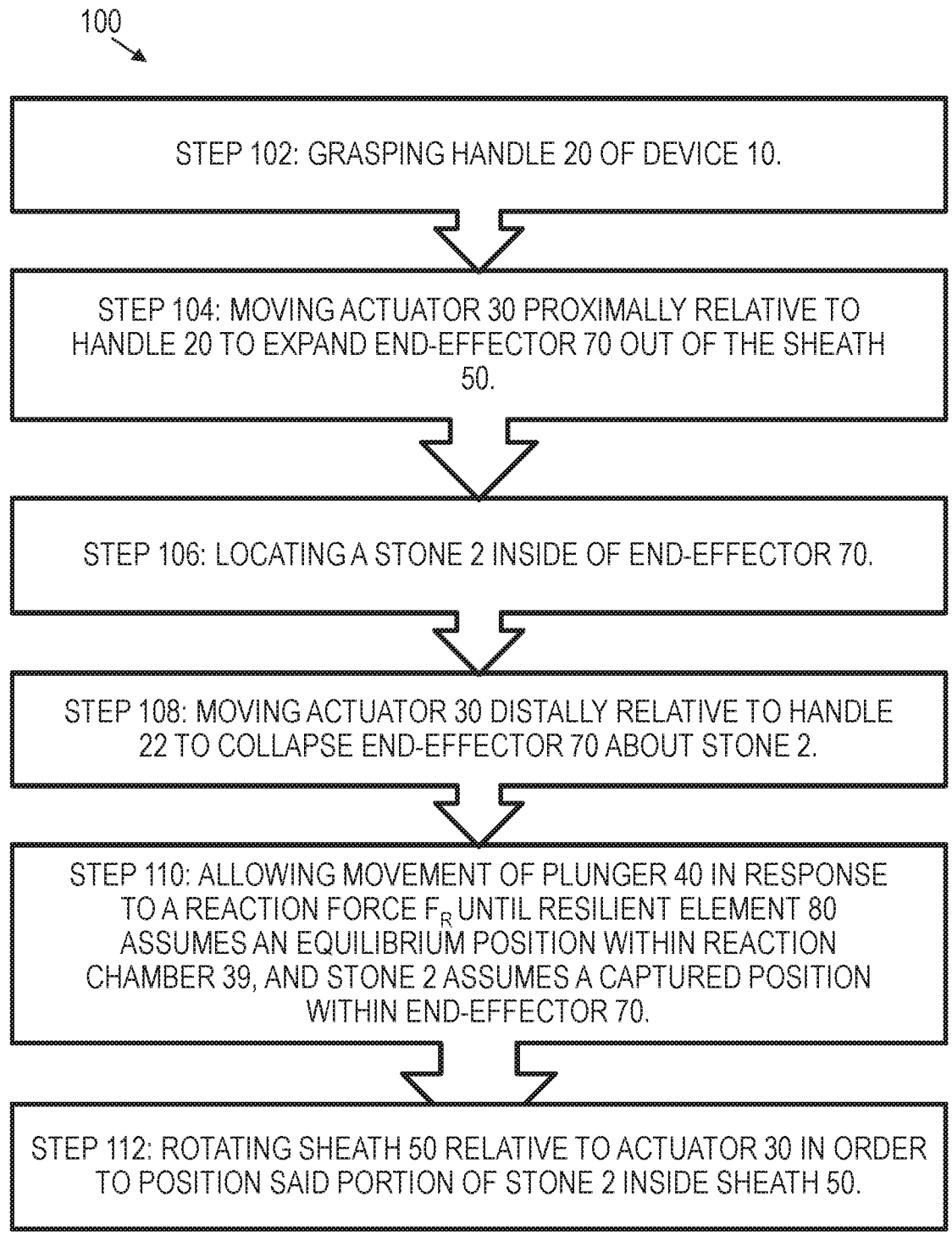
FIG. 5 depicts an exemplary method.

Aspects of a method 100 are now described with reference to a urology procedure where device 10 is utilized to capture a stone 2. An exemplary method 100 is depicted in FIG. 5; additional aspects of method 100 are depicted in FIGS. 3A-D. As shown, method 100 may comprise a step 102 of grasping handle 20 of device 10, as in FIG. 3A, wherein actuator 30 and end-effector 70 are in their respective closed configurations. Another step 104 may comprise moving actuator 30 proximally relative to handle 20 to expand end-effector 70 out of the sheath 50, as in FIG. 3B, wherein actuator 30 and end-effector 70 are in their respective open configurations. For example, actuator 30 may be moved by holding handle 20 in a fixed position with a hand of a user, and using a digit of said hand to apply a proximally-directed force $F_P$ to slider 36. Once end-effector 70 has been expanded, another method step 106 may comprise locating stone 2 inside of end-effector 70. For example, end-effector 70 may be a basket, and step 106 may comprise moving and/or rotating end-effector 70 (e.g., by moving and/or rotating handle 20) until stone 2 is located in the basket.

Method 100 of FIG. 5 includes additional steps for capturing stone 2. For example, another step 108 may comprise moving actuator 30 distally relative to handle 22 to collapse end-effector 70 about stone 2. As shown in FIG. 3C, for example, actuator 30 may be moved by holding handle 20 in the fixed position with the hand, and using a digit of said hand to apply a distally-directed force $F_P$ to slider 36. Slider 36 may be advanced distally without affecting sheath 50 and/or resilient element 80 until stone 2 begins to expand end-effector 70, at which point, a reaction force $F_R$ may be applied to sheath 50 by stone 2 and/or end-effector 70. As shown in FIG. 3D, for example, reaction force $F_R$ may have a proximally-directed component and a rotational component. Accordingly, method 100 may further comprise a step 110 allowing movement of plunger 40 in response to the reaction force $F_R$ until resilient element 80 assumes an equilibrium position within reaction chamber 39, and stone 2 assumes a stable, captured position within end-effector 70. Any aspect of force reduction element 90 described herein may support and/or be incorporated into step 108.

In some procedures, it may be desirable to capture at least a portion of stone 2 within a distal end 50D of sheath 50. Therefore, another method step 112 may comprise rotating sheath 50 relative to actuator 30 in order to position said portion of stone 2 inside distal end 50D. Step 112 may comprise applying said rotational forces to exterior handle surface 45 of distal stop 44D. For example, step 110 may be comprised of applying rotational forces to handle surface 45 in order to move stone 2 relative to end-effector 70. A back-and-forth rotational force may, for example, be applied to surface 45 to jiggle said portion of stone 2 into distal end 50D.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A device comprising:
   a handle including a wire attachment portion;
   an actuator movably mounted to the handle, the actuator including a reaction chamber;
   a plunger movably mounted to the actuator, the plunger including a distal stop with a sheath attachment portion, and a proximal stop located in the reaction chamber;
   a resilient element located in the reaction chamber, the resilient element including a proximal end movable relative to the plunger; and
   a force reduction element located in the reaction chamber between the proximal end of the resilient element and a proximal end of the reaction chamber, wherein the force reduction element includes an annular shape with an opening, and a shaft extending proximally from the proximal stop extends through the opening,
   wherein:
   the resilient element biases the plunger distally relative to the actuator;
   the resilient element is compressible when a proximally-directed force is applied to the plunger; and
   the force reduction element dissipates an amount of the proximally-directed force.

2. The device of claim 1, wherein the distal end of the resilient element is attached to the proximal stop.

3. The device of claim 1, wherein the force reduction element is movable relative to actuator and the resilient element.

4. The device of claim 3, wherein the force reduction element is movably mounted on the shaft.

5. The device of claim 1, wherein the actuator is made of a first material, the resilient element is made of a second material, the force reduction element is made of a third material, and a coefficient of friction between the first and second materials is greater than a coefficient of friction between the second and third materials.

6. The device of claim 5, wherein first material is polymeric and at least one of the second or third materials is metallic.

7. The device of claim 6, wherein the at least one of the second or third materials includes a lubricious coating or friction-reducing surface treatment.

8. The device of claim 1, wherein the plunger includes a body extending longitudinally between the proximal and distal stops, the distal end of the actuator includes an opening, and said body is movably mounted in said opening.

9. The device of claim 8, wherein an exterior guide surface of the body of the plunger is movable on an interior guide surface of the opening of the actuator, and at least one of said exterior and interior guide surfaces is configured to reduce an amount of the proximally-directed force required to move the plunger relative to the actuator.

10. A capture device comprising:
a handle including a wire attachment portion;
an actuator movably mounted to the handle, the actuator including a reaction chamber;
a plunger movably mounted to the actuator, the plunger including a distal stop with a sheath attachment portion, and a proximal stop located in the reaction chamber;
a shaft extending proximally from the proximal stop;
a sheath extending distally from the sheath attachment portion;
a wire extending distally from the wire attachment portion and through the actuator, the plunger, and the sheath;
an end-effector located at a distal end of the wire;
a resilient element located in the reaction chamber, the resilient element including a proximal end movable relative to plunger; and
a force reduction element located in the reaction chamber between the resilient element and a reaction surface of the reaction chamber, wherein the force reduction element includes an annular shape with an opening, and the shaft extends through the opening,
wherein:
the actuator is movable proximally relative to the handle to expand the end-effector out of the sheath, and distally relative to the handle to collapse the end-effector into the sheath;
the end-effector applies a proximally-directed force to the proximal end of the sheath when the actuator is moved distally to collapse the end effector around an object; and
the force reduction element dissipates of an amount of the proximally-directed force.

11. The device of claim 10, wherein:
prior to application of the proximally-directed force, the resilient element assumes an expanded configuration where (i) the proximal stop of the plunger maintains contact with a first reaction surface of the reaction chamber, (ii) the proximal end of the biasing element maintains contact with a distal surface of the force reduction element, and (iii) a proximal surface of the force reduction element maintains contacts with a second reaction surface of the reaction chamber; and
the actuator is movable relative to the handle to extend or collapse the end-effector without compressing the resilient element.

12. The device of claim 11, the proximally-directed force causes the resilient element to assume a compressed configuration where the distal stop is spaced apart from the first reaction surface.

13. The device of claim 12, wherein the force reduction element is movably mounted in the reaction chamber.

14. The device of claim 10, wherein a guide surface of the plunger is movable on a guide surface of the actuator, and at least one of said guide surfaces includes a lubricious coating or friction-reducing surface treatment.

15. The device of claim 10, further comprising a force transfer element attached to or embedded in a distal end of the sheath, wherein the force transfer element includes at least one of a ring, a coil, or a wire.

16. The device of claim 15, wherein the force transfer member is expandable with the distal end of the sheath.

17. A capture device comprising:
a handle including a wire attachment portion;
an actuator movably mounted to the handle, the actuator including a reaction chamber and a guide surface;
a plunger movably mounted to the actuator, the plunger including a distal stop with a sheath attachment portion, a proximal stop located in the reaction chamber, a guide surface movable on the guide surface of actuator, and a shaft extending proximally from the proximal stop;
a resilient element movably mounted on the shaft in the reaction chamber, the resilient element including a proximal end movable relative to the plunger and the shaft;
a sheath extending distally from the sheath attachment portion;
a wire extending distally from the wire attachment portion, through the shaft and the plunger, and into the sheath;
a basket located at a distal end of the wire; and
a force reduction element located in the reaction chamber between the resilient element and a reaction surface of the reaction chamber, wherein the force reduction element includes an annular shape with an opening, and the shaft extends through the opening,
wherein:
the actuator is movable proximally relative to the handle to expand the basket out of the sheath, and distally relative to the handle to collapse the basket into the sheath;
the basket applies a proximally-directed force to the sheath when the actuator is moved distally to collapse the basket around an object;
the sheath transfers the proximally-directed force to the plunger;
the plunger transfers the proximally-directed force into the resilient element; and
the force reduction element dissipates of an amount of the proximally-directed force.

18. The device of claim 17, wherein:
at least one of the guide surface of the actuator and the guide surface of the plunger is configured to reduce an amount of the proximally-directed force required to move the plunger relative to the actuator;
the sheath is configured to transfer the proximally directed force into the plunger without buckling; and
a distal end of the sheath is configured to transfer the proximally-directed force into the sheath without an expanding an outer diameter of said distal end.

* * * * *